US011497390B2

United States Patent
Kutsuma

(10) Patent No.: US 11,497,390 B2
(45) Date of Patent: Nov. 15, 2022

(54) ENDOSCOPE SYSTEM, METHOD OF GENERATING ENDOSCOPE IMAGE, AND PROCESSOR

(71) Applicant: OLYMPUS CORPORATION, Tokyo (JP)

(72) Inventor: Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 176 days.

(21) Appl. No.: 16/866,679

(22) Filed: May 5, 2020

(65) Prior Publication Data

US 2020/0260940 A1 Aug. 20, 2020

Related U.S. Application Data

(63) Continuation of application No. PCT/JP2018/030860, filed on Aug. 21, 2018.

(30) Foreign Application Priority Data

Nov. 9, 2017 (JP) .............................. JP2017-216159

(51) Int. Cl.
*A61B 1/05* (2006.01)
*A61B 1/06* (2006.01)
(Continued)

(52) U.S. Cl.
CPC ........ *A61B 1/0638* (2013.01); *A61B 1/00045* (2013.01); *A61B 1/000094* (2022.02);
(Continued)

(58) Field of Classification Search
CPC ............ A61B 1/00006; A61B 1/00009; A61B 1/00045; A61B 1/04; A61B 1/05;
(Continued)

(56) References Cited

U.S. PATENT DOCUMENTS

| 2012/0327205 A1* | 12/2012 | Takahashi .......... G02B 23/2461 |
| | | 348/65 |
| 2014/0031628 A1* | 1/2014 | Kaku .................... A61B 1/0638 |
| | | 600/178 |
| 2014/0049625 A1 | 2/2014 | Yokouchi et al. |
| 2015/0105758 A1* | 4/2015 | Igarashi ................. A61B 18/14 |
| | | 606/3 |

(Continued)

FOREIGN PATENT DOCUMENTS

| EP | 3132738 A1 | 2/2017 |
| EP | 3260035 A1 | 12/2017 |

(Continued)

OTHER PUBLICATIONS

International Search Report dated Oct. 9, 2018 issued in PCT/JP2018/030860.

*Primary Examiner* — Michael J Carey
*Assistant Examiner* — Julianna J Nicolaus
(74) *Attorney, Agent, or Firm* — Scully, Scott, Murphy & Presser, P.C.

(57) ABSTRACT

An endoscope apparatus includes a color image pickup device, a light source device configured to simultaneously illuminate the subject with light in a first wavelength band having a spectral characteristic of a narrow band having a peak in a range from a wavelength of 585 nm to a wavelength of 615 nm and light in a second wavelength band having a spectral characteristic for making, among a red signal, a green signal, and a blue signal, a pixel value of the red signal smallest, and a processor configured to assign either one of the red signal generated by return light from the subject illuminated with the light in the first wavelength band and the green signal or the blue signal generated by return light from the subject illuminated with the light in the second wavelength band to each of output channels corresponding to the respective colors in a display device.

13 Claims, 5 Drawing Sheets

(51) Int. Cl.
*A61B 1/00* (2006.01)
*G06T 7/00* (2017.01)

(52) U.S. Cl.
CPC .............. *A61B 1/05* (2013.01); *A61B 1/0646* (2013.01); *A61B 1/0655* (2022.02); *A61B 1/0661* (2013.01); *G06T 7/0012* (2013.01); *G06T 2207/10024* (2013.01); *G06T 2207/10068* (2013.01); *G06T 2207/30096* (2013.01)

(58) Field of Classification Search
CPC ....... A61B 1/042; A61B 1/045; A61B 1/0638; A61B 1/0646; A61B 1/0676; A61B 1/0684; G07T 2207/10024; G07T 2207/10068; G07T 2207/30101
See application file for complete search history.

(56) References Cited

U.S. PATENT DOCUMENTS

| | | |
|---|---|---|
| 2016/0306163 A1 | 10/2016 | Sakai et al. |
| 2018/0000335 A1 | 1/2018 | Igarashi et al. |
| 2019/0005641 A1* | 1/2019 | Yamamoto ............ G06T 7/0012 |

FOREIGN PATENT DOCUMENTS

| | | | |
|---|---|---|---|
| JP | H06-339459 A | 12/1994 | |
| JP | 2014-035759 A | 2/2014 | |
| JP | 5427318 B1 | 2/2014 | |
| WO | WO 2015/159676 A1 | 10/2015 | |
| WO | WO 2016/147436 A1 | 9/2016 | |
| WO | WO-2016147436 A1 * | 9/2016 | ......... H04N 9/04557 |

* cited by examiner

ENDOSCOPE SYSTEM, METHOD OF GENERATING ENDOSCOPE IMAGE, AND PROCESSOR

CROSS REFERENCE TO RELATED APPLICATION

This application is a continuation application of PCT/JP2018/030860 filed on Aug. 21, 2018 and claims benefit of Japanese Application No. 2017-216159 filed in Japan on Nov. 9, 2017, the entire contents of which are incorporated herein by this reference.

BACKGROUND OF THE INVENTION

1. Field of the Invention

The present invention relates to an endoscope system, a method of generating an endoscope image, and a processor, and particularly to an endoscope system capable of displaying a bleeding point inside a subject, a method of generating an endoscope image, and a processor.

2. Description of the Related Art

Conventionally, in a medical field, various types of minimally invasive inspections and surgeries using endoscopes have been performed. An operator can insert the endoscope into a body cavity, observe a subject, an image of which has been picked up by an image pickup apparatus provided in a distal end portion of an insertion section in the endoscope, and perform treatment for a lesion portion using a treatment instrument inserted into a treatment instrument channel, as needed. The surgery using the endoscope has an advantage of putting less physical burden on a patient because laparotomy or the like is not performed.

An endoscope apparatus is configured to include an endoscope, an image processing device connected to the endoscope, and an observation monitor. An image of a lesion portion is picked up by an image pickup device provided in a distal end portion of an insertion section in the endoscope, and the image is displayed on the monitor. An operator can perform a diagnosis or necessary treatment while viewing the image displayed on the monitor.

Some of endoscope apparatuses can perform not only normal light observation using white light but also special light observation using special light such as infrared light to observe an internal blood vessel.

For example, to perform treatment without damaging a blood vessel in a deeper portion of mucosa, a medicinal agent such as an indocyanine green (ICG) having an absorption peak characteristic in near-infrared light having a wavelength in the vicinity of 805 nm is intravenously injected, to display the blood vessel using an infrared endoscope apparatus. However, complicated work such as the intravenous injection of the medicinal agent is required.

Accordingly, Japanese Patent No. 5427318 proposes an endoscope apparatus that can clearly display a blood vessel in a deep portion of mucosa without performing complicated work such as administration of a medicinal agent. With the proposed endoscope apparatus, not only the blood vessel in the deep portion but also a bleeding point in a bleeding region at the time of bleeding can be identifiably displayed.

SUMMARY OF THE INVENTION

An endoscope system according to an aspect of the present invention includes a color image pickup device configured to receive light from a subject and generate image pickup signals respectively corresponding to a plurality of different colors, a light source device configured to simultaneously illuminate the subject with light in a first wavelength band having a spectral characteristic of a narrow band having a peak in a range from a wavelength of 585 nm to a wavelength of 615 nm and light in a second wavelength band having a spectral characteristic for making, among a red signal, a green signal, and a blue signal generated based on the image pickup signals respectively corresponding to the plurality of different colors, a pixel value of the red signal smallest, and a processor configured to assign either one of the red signal generated by the color image pickup device receiving return light from the subject illuminated with the light in the first wavelength band and the green signal or the blue signal generated by the color image pickup device receiving return light from the subject illuminated with the light in the second wavelength band to each of output channels corresponding to the respective colors in a display device configured to display a color image.

A method of generating an endoscope image according to an aspect of the present invention includes receiving light from a subject and generating image pickup signals respectively corresponding to a plurality of different colors, simultaneously illuminating the subject with light in a first wavelength band having a spectral characteristic of a narrow band having a peak in a range from a wavelength of 585 nm to a wavelength of 615 nm and light in a second wavelength band having a spectral characteristic for making, among a red signal, a green signal, and a blue signal generated based on the image pickup signals respectively corresponding to the plurality of different colors, a pixel value of the red signal smallest, and assigning either one of the red signal generated by the color image pickup device receiving return light from the subject illuminated with the light in the first wavelength band and the green signal or the blue signal generated by the color image pickup device receiving return light from the subject illuminated with the light in the second wavelength band to each of output channels corresponding to the respective colors in a display device configured to display a color image.

An endoscope system according to an aspect of the present invention includes a color image pickup device including a red pixel configured to output a red image pickup signal based on light transmitted by a red color filter, a green pixel configured to output a green image pickup signal based on light transmitted by a green color filter, and a blue pixel configured to output a blue image pickup signal based on light transmitted by a blue color filter, a light source device configured to simultaneously illuminate a subject with light in a first wavelength band having a spectral characteristic of a narrow band having a peak in a range from a wavelength of 585 nm to a wavelength of 615 nm and light in a second wavelength band having a spectral characteristic of a narrow band having a peak in a range from a wavelength of 400 nm to a wavelength of 585 nm, and a processor configured to respectively assign either one of a red image signal based on the red image pickup signal generated by the color image pickup device receiving returned light from the subject illuminated with the light in the first wavelength band and a green image signal based on the green image pickup signal generated by the color image pickup device receiving return light from the subject illuminated with the light in the second wavelength band to a red channel configured to output a red component, a green channel configured to output a green component, and a blue channel configured to output a blue component at each of pixels in a display device configured to display a color image.

A processor according to an aspect of the present invention is a processor to which an image signal including a red signal, a green signal, and a blue signal is inputted from an image pickup device, the processor being configured to control a light source to simultaneously illuminate a subject with light in a first wavelength band having a spectral characteristic of a narrow band having a peak in a range from a wavelength of 585 nm to a wavelength of 615 nm and light in a second wavelength band having a spectral characteristic for making a pixel value of the red signal in the image signal smallest, and assign either one of the red signal generated by the image pickup device receiving return light from the subject illuminated with the light in the first wavelength band and the green signal or the blue signal generated by the image pickup device receiving return light from the subject illuminated with the light in the second wavelength band to each of output channels corresponding to respective colors in a display device configured to display a color image.

and

Figure 6:
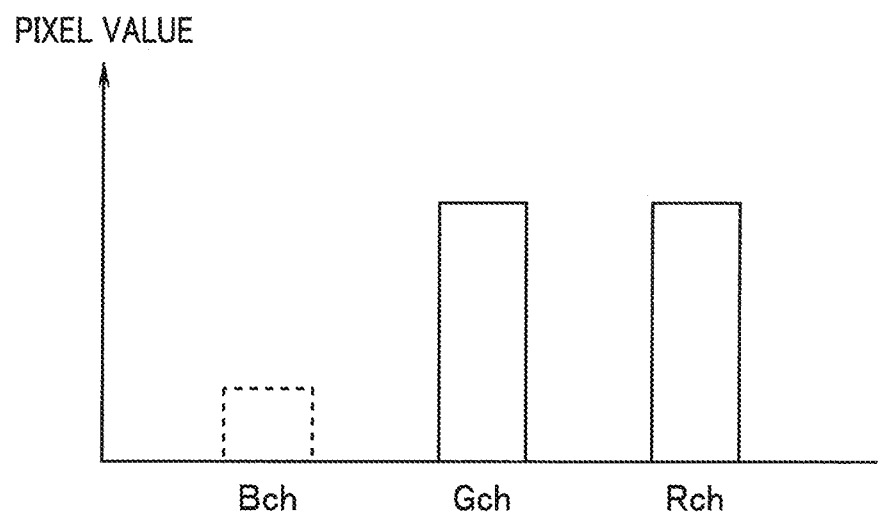

FIG. 6 is a graph illustrating an example of the magnitude of a pixel value of each of pixels in RGB colors to be inputted to the monitor 15 according to the embodiment of the present invention.

DETAILED DESCRIPTION OF THE PREFERRED EMBODIMENT

An embodiment of the present invention will be described below with reference to the drawings.

Figure 1:
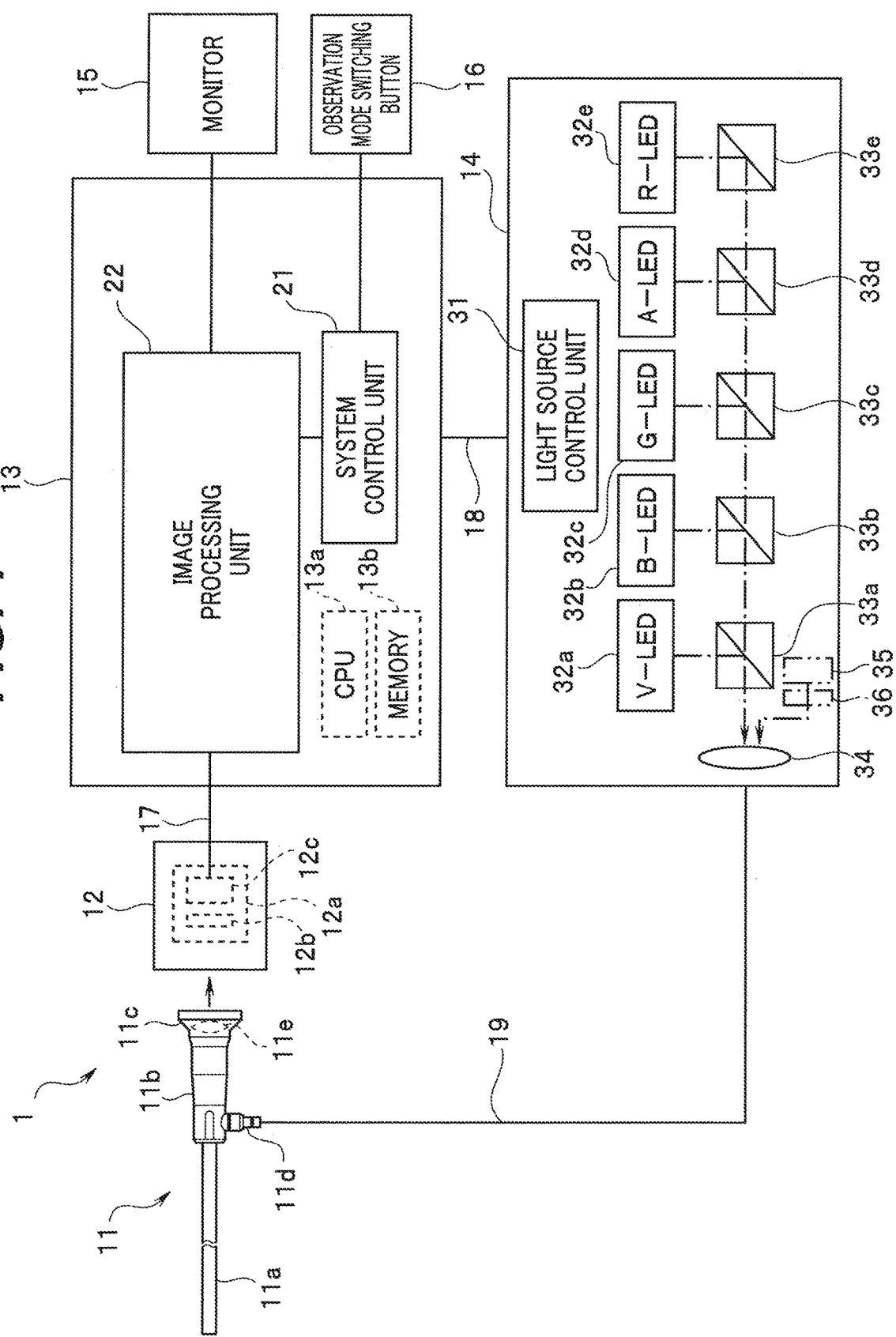
FIG. 1 is a configuration diagram illustrating a configuration of an endoscope apparatus including an image processing unit according to an embodiment of the present invention.

FIG. 1 is a configuration diagram illustrating a configuration of an endoscope apparatus including an image processing unit according to an embodiment.

An endoscope apparatus 1 includes an endoscope system configured to include a rigid endoscope 11, a camera head 12, a processor 13, a light source device 14, an observation monitor (hereinafter referred to as a monitor) 15, and an observation mode switching button 16. The camera head 12 is connected to the processor 13 via a cable 17. The processor 13 is connected to the light source device 14 via a cable 18.

The rigid endoscope 11 is a rigid endoscope including an elongated insertion section 11a, a grasping section 11b provided at a proximal end of the insertion section 11a, and an eyepiece section 11c provided in a proximal end portion of the grasping section 11b. The grasping section 11b is provided with a light guide connector 11d. The eyepiece section 11c contains a lens 11e. One end of the light guide cable 19 extending from the light source device 14 is connectable to the light guide connector 11d.

An observation window (not illustrated) and an illumination window (not illustrated) are provided in a distal end portion of the insertion section 11a. Light incident from the observation window is emitted from the lens 11e through an optical system such as a rod lens provided within the insertion section 11a. Illumination light from the light source device 14 is incident on the light guide connector 11d through a light guide within the light guide cable 19. The illumination light incident on the light guide connector 11d is emitted from the illumination window through an optical system such as a light guide provided within the insertion section 11a.

The eyepiece section 11c in the rigid endoscope 11 is mountable on the camera head 12, as indicated by an arrow.

The camera head 12 contains a lens system (not illustrated) and an image pickup unit 12a. The image pickup unit 12a has a light receiving surface for receiving light that has passed through the lens system, and includes an image pickup device 12b configured to photoelectrically convert an image of the received light and an image output unit 12c configured to process an output signal of the image pickup device 12b and output an image pickup signal as a digital signal.

The image pickup device 12b here is a CMOS image sensor including an on-chip color filter. The color filter is a filter in three primary colors RGB of light.

Note that the image pickup device 12b may be a CCD image sensor or the like, and the color filter may also be an image pickup device with a complimentary color filter.

From the foregoing, the image pickup device 12b is a (primary or complementary) color image pickup device configured to receive light from a subject and generate image pickup signals corresponding to a plurality of different colors.

Therefore, the rigid endoscope 11 and the camera head 12 constitute an endoscope including an image pickup device.

Note that the rigid endoscope 11 may be integral with the camera head 12 including the image pickup device 12b, although the rigid endoscope 11 is separate from the camera head 12 here.

Note that the endoscope may be a flexible endoscope including a flexible insertion section, although the endoscope is the rigid endoscope 11 here.

The image pickup unit 12a outputs an image pickup signal to the processor 13 via a signal line within the cable 17.

The processor 13 is an image processing device including a system control unit 21 and an image processing unit 22. The observation mode switching button 16 configured to switch an observation mode is connected to the processor 13.

The processor 13 includes a central processing unit (hereinafter referred to as a CPU) 13a and a memory 13b including a ROM, a flash memory, and the like. The memory 13b stores a software program and data for various types of functions of the system control unit 21 and a software program and data for various types of processing of the image processing unit 22. When the CPU 13a reads out a necessary program and data from the memory 13b and executes the read program and data in response to an instruction from a user, various types of functions and various types of processing are performed.

The system control unit 21 controls the image pickup unit 12a in the camera head 12, the image processing unit 22, and the light source device 14.

The processor 13 includes an operation panel not illustrated, and the user, i.e., an operator or a nurse, for example, can set or change an operation mode of the endoscope apparatus 1 and perform various types of instructions and various types of adjustments by operating the operation panel and the observation mode switching button 16.

Accordingly, the system control unit 21 controls an entire operation of the endoscope apparatus 1 by the CPU 13a reading out a program corresponding to the instruction from the user from the memory 13b and executing the read program and controls the image pickup unit 12a and the light source device 14 corresponding to the observation mode in response to the instruction from the user.

The image processing unit 22 receives an image pickup signal from the image pickup unit 12a, to perform various types of image processing for the image pickup signal.

The endoscope apparatus 1 has two observation modes, here, a normal light observation mode and a bleeding point observation mode.

The normal light observation mode is a mode for generating an image as a subject image obtained by reflected light from the subject and outputting an image signal of the image to the monitor 15 when the subject is irradiated with white light. Although white light is not emitted from the light source device 14 in the present embodiment, a plurality of narrowband lights are emitted, to generate an image when the subject is irradiated with similar illumination light to white light.

The bleeding point observation mode is a mode for irradiating the subject with one or two or more predetermined narrowband lights (here, two narrowband lights) to generate an image as a subject image obtained by reflected light of the narrowband light and outputting an image signal of the image to the monitor 15 to display a bleeding point of the subject. The bleeding point observation mode is used in confirming a place where bleeding has occurred, i.e., a bleeding point when a mucosal surface is covered with blood.

The observation mode switching button 16 is connected to the system control unit 21. The user can select the desired observation mode out of the two observation modes by operating the observation mode switching button 16.

Note that the observation mode switching button 16 may be provided in an operation panel (not illustrated) of the processor 13, although the observation mode switching button 16 here is an independent operation member.

Although the endoscope apparatus 1 here has the two observation modes, i.e., the normal light observation mode and the bleeding point observation mode, the endoscope apparatus 1 may have a narrowband light observation mode for irradiating the subject with one or two or more predetermined narrowband lights of each of light sources 32a to 32e to generate an image as a subject image obtained by reflected light of the narrowband light and outputting an image signal of the image to the monitor 15 to observe a capillary blood vessel on a mucosal surface layer.

An observation mode signal representing the observation mode selected by the observation mode switching button 16 is inputted to the system control unit 21. The system control unit 21 feeds a control signal corresponding to the observation mode signal to the image processing unit 22.

The image processing unit 22 processes an image pickup signal based on the control signal from the system control unit 21, to generate an endoscope image signal and output the generated endoscope image signal to the monitor 15. In other words, the image processing unit 22 performs image processing corresponding to the observation mode.

The light source device 14 includes the light source control unit 31, the plurality of (here, five) light sources 32a, 32b, 32c, 32d, and 32e, a plurality of (here, five) mirrors 33a, 33b, 33c, 33d, and 33e, and a light collecting lens 34.

The light source control unit 31 includes a CPU, a ROM, and a RAM, and controls each of the units in the light source device 14 based on a control signal from the processor 13 via a signal line within the cable 18.

The light source 32a is a light emitting diode (hereinafter referred to as an LED) (V-LED) configured to emit narrowband light having a center wavelength of 410 nm and having a full width at half maximum of 10 nm. The light source 32a is a light emitting element configured to emit violet narrowband light. Light to be emitted from the light source 32a is transmitted by a blue portion of the color filter in the image pickup device 12b in the image pickup unit 12a. In other words, the light source 32a emits narrowband light NBL1 having a center wavelength of 410 nm.

The light source 32b is an LED (B-LED) configured to emit narrowband light having a center wavelength of 460 nm and having a full width at half maximum of 10 nm. The light source 32b is a light emitting element configured to emit blue narrowband light. Light to be emitted from the light source 32b is transmitted by a blue portion of the color filter in the image pickup device 12b in the image pickup unit 12a. In other words, the light source 32b emits narrowband light NBL2 having a center wavelength of 460 nm.

The light source 32c is an LED (G-LED) configured to emit narrowband light having a center wavelength of 540 nm and having a full width at half maximum of 30 nm. The light source 32c is a light emitting element configured to emit green narrowband light. Light to be emitted from the light source 32c is transmitted by a green portion of the color filter in the image pickup device 12b in the image pickup unit 12a. In other words, the light source 32c emits narrowband light NBL3 having a center wavelength of 540 nm.

The light source 32d is an LED (A-LED) configured to emit narrowband light having a center wavelength of 600 nm and having a full width at half maximum of 10 nm. The light source 32d is a light emitting element configured to emit red narrowband light. Light to be emitted from the light source 32d is transmitted by a red portion of the color filter in the image pickup device 12b in the image pickup unit 12a. In other words, the light source 32d emits narrowband light NBL4 having a center wavelength of 600 nm.

Note that although the light source 32d here emits the narrowband light having a center wavelength of 600 nm and having a full width at half maximum of 10 nm, the narrowband light may be light in a wavelength band having a spectral characteristic of a narrow band having a peak in a range from a wavelength of 585 nm to a wavelength of 615 nm.

The light source 32e is an LED (R-LED) configured to emit narrowband light having a center wavelength of 630 nm and having a full width at half maximum of 10 nm. The light source 32e is a light emitting element configured to emit red narrowband light. Light to be emitted from the light source 32d is transmitted by the red portion of the color filter in the image pickup device 12b in the image pickup unit 12a. In other words, the light source 32e emits narrowband light NBL5 having a center wavelength of 630 nm.

Note that while each of the light sources here is an LED, all or some of the plurality of light sources may be each a combination of a laser diode and a fluorescent substance.

Each of the mirrors 33a, 33b, 33c, 33d, and 33e is a dichroic mirror.

The mirror 33a is an optical material configured to reflect the narrowband light NBL1 having a center wavelength of 410 nm and transmit lights having other wavelengths on an internal mirror surface.

The mirror 33b is an optical material configured to reflect the narrowband light NBL2 having a center wavelength of 460 nm and transmit lights having other wavelengths on an internal mirror surface.

The mirror 33c is an optical material configured to reflect the narrowband light NBL3 having a center wavelength of 540 nm and transmit lights having other wavelengths on an internal mirror surface.

The mirror 33d is an optical material configured to reflect the narrowband light NBL4 having a center wavelength of 600 nm and transmit lights having other wavelengths on an internal mirror surface.

The mirror 33e is an optical material configured to reflect the narrowband light NBL5 having a center wavelength of 630 nm and transmit lights having other wavelengths on an internal mirror surface.

Accordingly, the narrowband light NBL1 emitted from the light source 32a is reflected on the mirror 33a and is directed toward the light collecting lens 34. The narrowband light NBL2 emitted from the light source 32b is reflected on the mirror 33b, and is transmitted by the mirror 33a and directed toward the light collecting lens 34. The narrowband light NBL5 emitted from the light source 32c is reflected on the mirror 33c, and is transmitted by the mirrors 33a and 33b and directed toward the light collecting lens 34. The narrowband light NBL4 emitted from the light source 32d is reflected on the mirror 33d, and is transmitted by the mirrors 33a, 33b, and 33c and directed toward the light collecting lens 34. The narrowband light NBL5 emitted from the light source 32e is reflected on the mirror 33e, and is transmitted by the mirrors 33a, 33b, 33c and 33d, and directed toward the light collecting lens 34.

The light collecting lens 34 collects respective lights from the five mirrors 33a to 33e on a proximal end surface of the light guide within the light guide cable 19. The light from the light collecting lens 34 is emitted from a distal end surface of the light guide within the light guide cable 19, and is supplied to the rigid endoscope 11 via the light guide connector 11d. The light incident on the light guide connector 11d is emitted as illumination light from the illumination window of the insertion section 11a.

At the time of the normal light observation mode, currents are respectively supplied to the five light sources 32a, 32b, 32c, 32d, and 32e, and the five narrowband lights NBL1, NBL2, NBL3, NBL4, and NBL5 are simultaneously emitted from the light source device 14.

At the time of the bleeding point observation mode, currents are respectively supplied to the two light sources 32c and 32d, and the narrowband light NBL3 and the narrowband light NBL4 are simultaneously emitted from the light source device 14. In other words, at the time of the bleeding point observation mode, the light source device 14 constitutes an illumination unit configured to simultaneously illuminate the subject with light in a first wavelength band having a spectral characteristic of a narrow band having a peak in a range from a wavelength of 585 nm to a wavelength of 615 nm and light in a second wavelength band having a spectral characteristic for making, among a red signal, a green signal, and a blue signal, the subject most difficult to display on the red signal.

The light source device 14 as an illumination unit illuminates the subject with light having a spectral characteristic having a peak in a range from a wavelength of 400 nm to a wavelength of 585 nm as the light in the second wavelength band simultaneously with the light in the first wavelength band.

Since entire processing in the normal light observation mode is similar to the entire processing in the conventional example, description of the entire processing is omitted, and processing in the bleeding point observation mode will be described.

Figure 2:
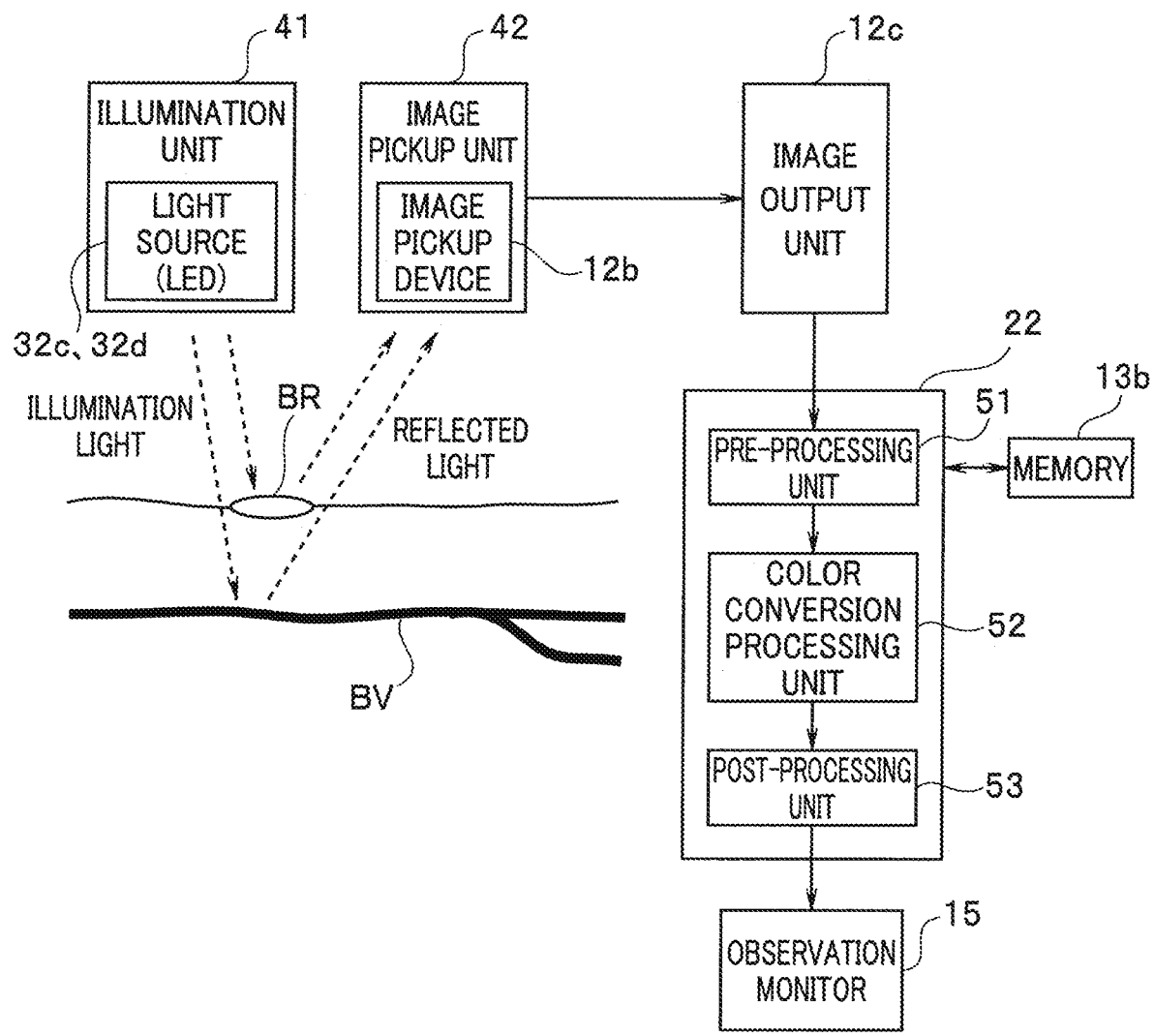
FIG. 2 is a diagram for describing a flow of entire processing in bleeding point observation according to the embodiment of the present invention.

FIG. 2 is a diagram for describing a flow of entire processing in bleeding point observation according to the present embodiment.

The operator inserts the insertion section in the endoscope into a body cavity, and positions the distal end portion of the insertion section in the endoscope in the vicinity of a lesion portion under the normal light observation mode. The operator operates the observation mode switching button 16 to observe a bleeding point when the operator confirms bleeding, and switches the observation mode of the endoscope apparatus 1 to the bleeding point observation mode, although the operator performs necessary treatment while confirming the lesion portion to be treated.

Under the bleeding point observation mode, the system control unit 21 in the processor 13 controls the light source device 14, to drive the two light sources 32c and 32d and simultaneously emit the narrowband light NBL3 having a center wavelength of 540 nm and the narrowband light NBL4 having a center wavelength of 600 nm, as described above. Further, the system control unit 21 controls the image processing unit 22, to perform image processing for bleeding point observation.

As illustrated in FIG. 2, in the bleeding point observation mode, respective illumination lights having two narrow band wavelengths from an illumination unit 41 are emitted from the distal end portion of the insertion section 11a in the rigid endoscope 11, and is irradiated onto an observation region. Here, the observation region is a region including a bleeding point in the vicinity of a lesion portion in a body cavity. In the observation region, a blood vessel BV exists on a mucosal surface layer. In particular, the blood vessel BV is a capillary blood vessel.

The illumination unit 41 includes the light sources 32c and 32d and an illumination optical system. The illumination optical system includes the light guide cable 19 and the light guide and the illumination window of the insertion section 11a within the rigid endoscope 11. The illumination unit 41 emits the narrowband light NBL3 in the vicinity of a wavelength of 540 nm and the narrowband light NBL4 in the vicinity of a wavelength of 600 nm.

Respective reflected lights from observation regions of the narrowband lights NBL3 and NBL4 are received by the image pickup unit 42. The image pickup unit 42 includes the image pickup device 12b and an image pickup optical system. The image pickup optical system includes the rod lens within the insertion section 11a and the lens 11e. The respective reflected lights of the narrowband lights NBL3 and MBL4 are received by the image pickup device 12b. The image pickup device 12b outputs an image pickup signal of the reflected light to the image output unit 12c.

The image output unit 12c is a circuit including an analog front-end circuit (AFE) or the like, and generates an image signal as a digital signal from an output signal of the image pickup device 12b and outputs the generated image signal to the processor 13. The image signal is received by the image processing unit 22 in the processor 13.

The image processing unit 22 in the processor 13 includes a pre-processing unit 51, a color conversion processing unit 52, and a post-processing unit 53.

The pre-processing unit 51 performs pre-processing such as white spot correction and demosaicking processing, and outputs an image signal in a predetermined format such as an RGB or YC format. Here, the image signal in the RGB format is outputted from the pre-processing unit 51.

The color conversion processing unit 52 performs color conversion processing for the image signal. For example, color conversion processing using a color matrix is performed in the color conversion processing unit 52. At the time of the bleeding point observation mode, the color conversion processing unit 52 is used to adjust a color tone of blood.

Note that nine-axis color adjustment processing or the like may be performed in addition to the color conversion processing using the color matrix. For example, color assignment to output channels in the monitor 15 and gain correction for each color may be performed by the color conversion processing using the color matrix, and color adjustment in a specific color space may be performed by the nine-axis color adjustment processing.

When the color matrix is used, for example, three image signals in RGB colors to be inputted to the color conversion processing unit 52 are respectively color-converted into three image signals in RGB colors by the color matrix. The input image signals are respectively an image signal Rin in red (R), an image signal Gin in green (G), and an image signal Bin in blue (B). The input image signals are respectively converted into output image signals by a matrix C. When it is assumed that the output image signals are respectively the image signal Rout in red (R), the image signal Gout in green (G), and the image signal Bout in blue (B), the output image signals are expressed by the following equation (1).

$$\begin{bmatrix} Rout \\ Gout \\ Bout \end{bmatrix} = \begin{bmatrix} C_{00} & C_{01} & C_{02} \\ C_{10} & C_{11} & C_{12} \\ C_{20} & C_{21} & C_{22} \end{bmatrix} \begin{bmatrix} Rin \\ Gin \\ Bin \end{bmatrix} \quad (1)$$

The matrix C is a color matrix with three rows and three columns. Each of the image signals Rin, Gin, and Bin is a pixel value.

Setting of nine coefficients C00 to C22 in the matrix C can be changed. The user can change the setting of each of the coefficients by operating the operation panel not illustrated. When each of the coefficients in the matrix C is set, the image signals Rin, Gin, and Bin can be respectively assigned to the output channels in the monitor 15, and a color tone of a color of blood, a color of a bleeding point, or the like to be displayed can be set to a desired color tone.

The color conversion processing unit 52 constitutes an assignment unit configured to respectively assign, among a red signal corresponding to red, a green signal corresponding to green, and a blue signal corresponding to blue that are generated from the image pickup signals corresponding to the plurality of different colors generated by the color image pickup device, the red signal and at least one of the green signal and the blue signal to the output channels corresponding to the respective colors in the monitor 15 as a display unit configured to display a color image.

As described below, in the present embodiment, the image signal Rin as the red signal is assigned to a red channel and a green channel among the output channels in the monitor 15, and the image signal Gin as the green signal is assigned to a blue channel among the output channels in the monitor 15.

The post-processing unit 53 performs post-processing such as various types of enhancement processing and size conversion processing, and outputs an image signal, which has been subjected to various types of processing, to the monitor 15.

As described above, through color conversion by the color conversion processing unit 52 in the image processing unit 22, the image signals Rin, Gin, and Bin are assigned to the respective output channels in RGB colors in the monitor 15. As a result, a bleeding point BP within a bleeding region BR is displayed on a screen 15a of the monitor 15 with good visibility. Accordingly, the operator can quickly and appropriately subject the bleeding point BP to hemostasis processing while viewing a video displayed on the monitor 15.

Figure 3:
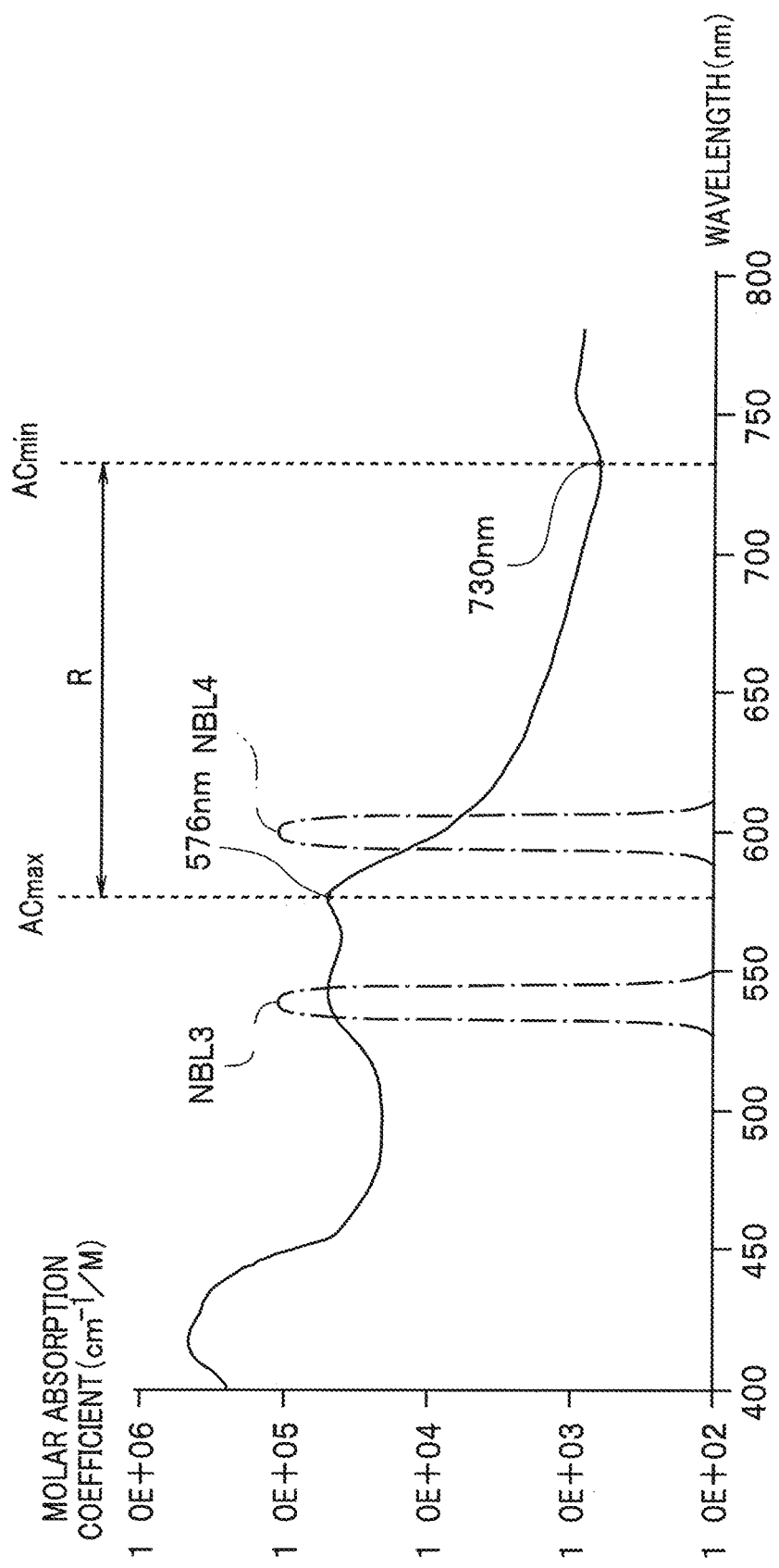
FIG. 3 is a diagram illustrating a light absorption characteristic of venous blood according to the embodiment of the present invention.

A light absorption characteristic of venous blood will be described. FIG. 3 is a diagram illustrating a light absorption characteristic of venous blood. A vertical axis and a horizontal axis in FIG. 3 respectively indicate a molar absorption coefficient (cm-1/M) and a wavelength. Note that although illumination lights as two narrowband lights are also affected by a scattering characteristic of a living tissue itself, the scattering characteristic of the living tissue itself substantially monotonously decreases as the wavelength increases. Thus, FIG. 3 will be described as an absorption characteristic of the living tissue.

Generally, oxygenated hemoglobin ($HbO_2$) and reduced hemoglobin (Hb) (hereinafter collectively merely referred to as hemoglobin) are contained in a ratio of approximately 60:40 in venous blood. Although light is absorbed by hemoglobin, an absorption coefficient of the hemoglobin differs for each wavelength of the light. FIG. 3 illustrates a light absorption characteristic of venous blood for each wavelength from 400 nm to approximately 800 nm, and the absorption coefficient represents a maximal value at a point corresponding to a wavelength of approximately 576 nm and represents a minimal value at a point corresponding to a wavelength of 730 nm.

In the bleeding point observation mode, two narrowband lights are irradiated, and respective return lights are received in the image pickup device 12b.

The narrowband light NBL4 in the vicinity of a wavelength of 600 nm is wavelength band light within a wavelength band R from a maximal value ACmax (here, an absorption coefficient in a wavelength of 576 nm) to a minimal value ACmin (here, an absorption coefficient in a wavelength of 730 nm) of an absorption characteristic of hemoglobin.

In other words, the light source device 14 irradiates the narrowband light NBL4 as first illumination light having a peak wavelength of a spectral characteristic between a wavelength band including the maximal value ACmax and a wavelength band in the minimal value ACmin in the absorption characteristic of the living tissue.

Further, the light source device 14 also irradiates the narrowband light NBL3 in the vicinity of a wavelength of 540 nm. The second narrowband light NBL3 is light in a wavelength band outside the wavelength band R from the maximal value ACmax to the minimal value ACmin in the absorption characteristic of hemoglobin and is illumination light that can be transmitted by a predetermined distance from a surface layer portion of the mucosal surface of the subject.

The image pickup device 12b outputs an image pickup signal of each of images of the two narrowband lights.

Accordingly, each of the images includes a plurality of pixel signals based on each of respective return lights of the first and second narrowband lights NBL4 and NBL3.

Figure 4:
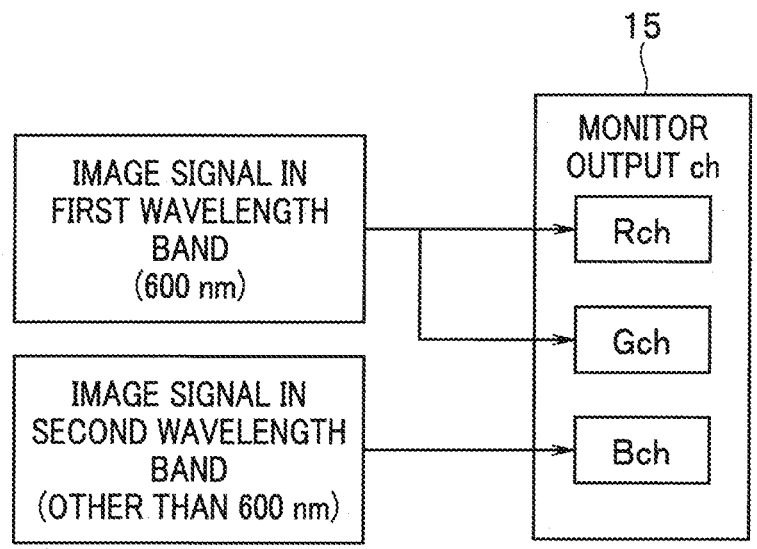
FIG. 4 is a diagram for describing channel assignment of two image signals at the time of a bleeding point observation mode according to the embodiment of the present invention.

FIG. 4 is a diagram for describing channel assignment of two image signals at the time of the bleeding point observation mode.

As illustrated in FIG. 4, at the time of the bleeding point observation mode, an image signal G1 in a first wavelength band in the vicinity of a wavelength of 600 nm is assigned to a red channel (Rch) and a green channel (Gch) in the monitor 15, and an image signal G2 in a second wavelength band in the vicinity of a wavelength of 540 nm is assigned to a blue channel (Bch) in the monitor 15.

In other words, the color conversion processing unit 52 as an assignment unit assigns the red signal to the red channel and the green channel among the output channels corresponding to the respective colors in the monitor 15, and assigns the green signal to the blue channel among the output channels corresponding to the respective colors.

Normally, blood appears red under white light. Thus, the channel assignment as illustrated in FIG. 4 is performed such that blood is displayed in a yellowish or orangish color.

Further, the color conversion processing unit 52 can also perform gain adjustment of each of the image signals to be respectively inputted to the color channels by adjusting each of the coefficients in the matrix C together with the channel assignment illustrated in FIG. 4.

In other words, the color conversion processing unit 52 can respectively assign the red signal assigned to the red channel (Rch) and the red signal assigned to the green channel (Gch) in the monitor 15 to the output channels corresponding to the respective colors by multiplying the red signals by a gain such that a color image to be displayed on the monitor 15 as a display unit is displayed in yellow by using the above-described matrix C. Thus, respective color tones of blood and a bleeding point can be set as desired color tones.

Note that color tones may be adjusted by nine-axis color adjustment or other adjustment methods, as described above.

Figure 5:
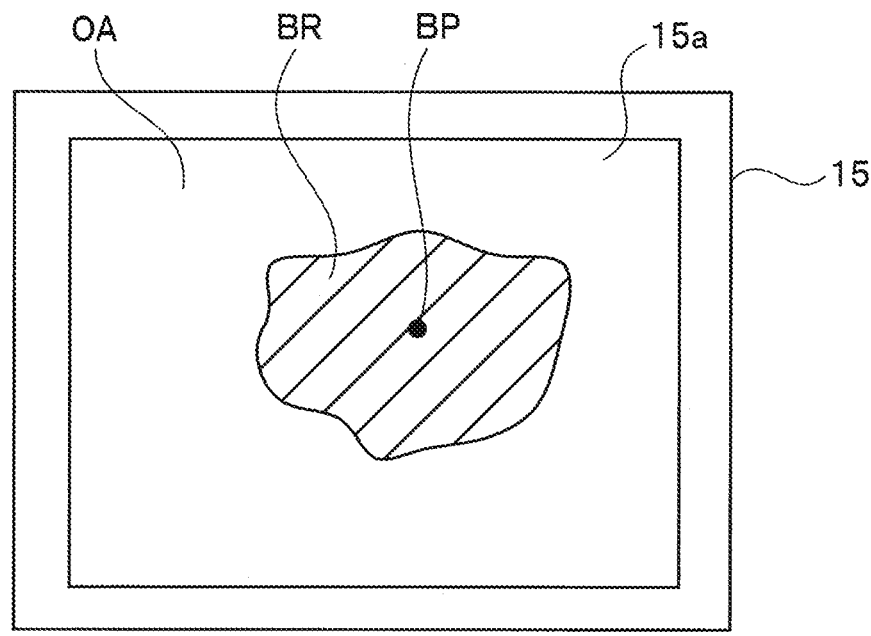
FIG. 5 is a diagram illustrating an example of an image to be displayed on a display screen of a monitor 15 according to the embodiment of the present invention.

FIG. 5 is a diagram illustrating an example of an image to be displayed on the display screen of the monitor 15.

FIG. 5 indicates that the bleeding region BR on the mucosal surface is displayed in the screen 15a of the monitor 15.

By the above-described channel assignment, a region OA other than the bleeding region BR is displayed in a whitish color, the bleeding region BR is displayed in yellow, and the bleeding point BP in the bleeding region is displayed in dark yellow or in orange.

When coefficients in the above-described matrix C are adjusted so that there is no difference between a signal to be inputted to the R channel and a signal to be inputted to the G channel in the monitor 15, for example, the bleeding point is displayed in predetermined yellow. However, when the signal to be inputted to the R channel is made larger than the signal to be inputted to the G channel, redness of the color of the bleeding point can be heightened.

Note that the coefficients in the matrix C are also set in consideration of correction by y (gamma) processing and a color balance between the light sources 32c and 32d.

Each of the set coefficients in the matrix C is stored in a rewritable storage device such as a flash memory in the memory 13b, and can be referred to, i.e., can be read out by the image processing unit 22.

FIG. 6 is a graph illustrating an example of the magnitude of a pixel value of each of pixels in RGB colors to be inputted to the monitor 15.

Although the image signal in the first wavelength band is fed to the red channel (Rch) and the green channel (Gch) among the output channels in the monitor 15, and the image signal in the second wavelength band is fed to the blue channel (Bch) among the output channels in the present embodiment, illumination light here does not include blue (B). Thus, a pixel value to be fed to the blue channel (Bch) is a value close to almost zero, as illustrated in FIG. 6.

On the other hand, both pixel values of image signals in the first wavelength band to be respectively fed to the red channel (Rch) and the green channel (Gch) among the output channels in the monitor 15 are large. Accordingly, a color of the bleeding point within an endoscope image can be set to a desired yellow color tone by adjusting the coefficients in the color matrix.

Note that when narrowband lights respectively having center wavelengths of 410 nm and 460 nm are used as the second wavelength band, respective color tones of the bleeding point, the bleeding region, and the region other than the bleeding region can be set to desired color tones by setting the pixel value to the blue channel Bch in the monitor 15 to a value exceeding zero to adjust the coefficients in the matrix C.

When indigo carmine or the like is scattered or locally injected, for example, adjustment of an intensity or a color tone performed when indigo carmine is displayed on the blue channel Bch can also be performed by adjusting the coefficients in the matrix C.

As described above, according to the above-described embodiment, there can be provided an endoscope system capable of displaying an image having high visibility of a bleeding point in a bleeding region.

Since narrowband lights in two wavelength bands are used, an image of a bleeding point can be displayed by a color image.

Particularly, when two narrowband lights are color-converted, a color tone of entire blood can be set to a desired color tone and a color tone of a bleeding point can also be displayed with high contrast by adjusting coefficients, for example.

Modification 1

Note that although the narrowband light NBL3 having a center wavelength of 540 nm is used as light in a wavelength band having a spectral characteristic for making a subject most difficult to display on a red signal in the above-described embodiment, narrowband light NBL1 having a center wavelength of 410 nm or narrowband light NBL2 having a center wavelength of 460 nm may be used.

Alternatively, at least two of narrowband light NBL1 having a center wavelength of 410 nm, narrowband light NBL2 having a center wavelength of 460 nm, and narrowband light NBL3 having a center wavelength of 540 nm may be used instead of narrowband light NBL3 having a center wavelength of 540 nm as light in a wavelength band having a spectral characteristic for making a subject most difficult to display on a red signal.

In other words, light in a wavelength band in a range from a wavelength of 400 nm to a wavelength of 585 nm may be used as light in a wavelength band having a spectral characteristic for making a subject most difficult to display on a red signal.

Further, a light source device 14 may simultaneously irradiate a subject with light in a wavelength band different from the narrowband light NBL3 having a center wavelength of 540 nm, e.g., the narrowband light NBL1 having a center wavelength of 410 nm or the narrowband light NBL2 having a center wavelength of 460 nm together with the narrowband light NBL3 having a center wavelength of 540 nm as light in a wavelength band having a spectral characteristic for making the subject most difficult to display on a red signal, to drive a light source 32a or 32b, a light source 32c, and a light source 32d and simultaneously emit three lights at the time of a bleeding point observation mode.

Modification 2

Note that although the light source device 14 uses five light sources as light emitting elements respectively configured to emit a plurality of narrowband lights in the above-described embodiment, one light source configured to emit white light and a band limitation unit may be used.

Although the light source device 14 includes the light source 32d configured to emit light in a first wavelength band and the light source 32c configured to emit light in a second wavelength band in the above-described embodiment, a light source device 14 includes one light source 35 and a bimodal filter 36 as a band limitation unit, as each indicated by a dotted line in FIG. 1, in a modification 2.

The bimodal filter 36 transmits narrowband light having a center wavelength of 600 nm and light in a wavelength band (e.g., narrowband light NBL3) having a spectral characteristic for making a subject most difficult to display on a red signal.

In the case, the bimodal filter 36 deviates from an optical path of illumination light, and light to be emitted by the light source 35 of white light is emitted as illumination light to a light collecting lens 34 at the time of a normal light observation mode, and light to be emitted by the light source 35 of white light is emitted toward the bimodal filter 36, and light transmitted by the bimodal filter 36 is emitted as illumination light to the light collecting lens 34 at the time of a bleeding point observation mode.

In other words, the light source device 14 as an illumination unit may include a light source configured to emit light in a wide wavelength band including light in a first wavelength band (the narrowband light NBL4 in the above-described embodiment) and light in a second wavelength band (the narrowband light NBL3 in the above-described embodiment) and the bimodal filter 36 as a band limitation unit configured to perform band limitation to transmit only the lights in the two wavelength bands, i.e., the first wavelength band and the second wavelength band, and the light in the first wavelength band and the light in the second wavelength band may be simultaneously emitted from the light source through the bimodal filter 36.

Modification 3

Although the narrowband light NBL4 having a center wavelength of 600 nm is irradiated as illumination light onto a subject in the above-described embodiment or the modification 2, an image signal obtained by spectral estimation (a similar signal to an image signal obtained by narrowband light NBL4 having a center wavelength of 600 nm) may be used using narrowband light other than the narrowband light NBL4 as illumination light based on an image signal obtained from reflected light obtained from the narrowband light.

As illustrated in FIG. 3, an image signal having a center wavelength of 600 nm is obtained from the obtained image signal by spectral estimation processing using narrowband light NBL5 that greatly changes in absorption characteristic as illumination light, like the narrowband light NBL4, and then similar processing to the processing in the above-described embodiment is performed.

In the case, the light source device 14 illustrated in FIG. 1 does not include a light source 32d.

As described above, according to the above-described embodiment and modifications, there can be provided an endoscope system capable of displaying an image having high visibility of a bleeding point in a bleeding region, a method of generating an endoscope image, and a processor.

The present invention is not limited to the above-described embodiment, but various changes, alterations, and the like are possible without departing from the scope and spirit of the invention.

What is claimed is:

1. An endoscope system comprising:
 a color image sensor configured to receive light from a subject and generate image pickup signals respectively corresponding to a plurality of different colors;
 a light source configured to simultaneously illuminate the subject with light in a first wavelength band having a spectral characteristic of a narrow band having a peak in a range from a wavelength of 585 nm to a wavelength of 615 nm and light in a second wavelength band having a spectral characteristic for making, among a red signal, a green signal, and a blue signal generated based on the image pickup signals respectively corresponding to the plurality of different colors, a pixel value of the red signal smallest; and
 a processor configured to:
  receive a selection signal of a specified observation mode; and
  in response to receiving the selection signal of the specified observation mode:
   assign the red signal generated by the color image sensor receiving return light from the subject illuminated with the light in the first wavelength band to a red channel and a green channel of output channels corresponding to the respective colors in a display configured to display a color image; and
   assign the green signal or the blue signal generated by the color image sensor receiving return light from the subject illuminated with the light in the second wavelength band to a blue channel among the output channels corresponding to the respective colors in the display configured to display the color image.

2. The endoscope system according to claim 1, wherein the light source is configured to illuminate the subject with light having a spectral characteristic having a peak in a range from a wavelength of 400 nm to a wavelength of 585 nm as the light in the second wavelength band simultaneously with the light in the first wavelength band.

3. The endoscope system according to claim 1 wherein the processor is configured to, in response to receiving the selection of the specified observation mode, assign the red signal assigned to the red channel and the red signal assigned to the green channel to the output channels corresponding to the respective colors by multiplying the red signals by a gain such that the color image displayed on the display is displayed in yellow.

4. The endoscope system according to claim 1,
wherein the light source is configured to emit light in a wavelength band including the first wavelength band and the second wavelength band,
wherein the endoscope system comprises a filter configured to perform band limitation to transmit only lights in two wavelength bands, that is, the first wavelength band and the second wavelength band, and
wherein the light in the first wavelength band and the light in the second wavelength band are simultaneously emitted from the light source through the filter.

5. The endoscope system according to claim 4,
wherein the filter is a bimodal filter.

6. The endoscope system according to claim 1,
wherein the light source comprises:
   a first light source configured to emit the light in the first wavelength band; and
   a second light source configured to emit the light in the second wavelength band.

7. The endoscope system according to claim 6,
wherein the light source comprises a third light source configured to emit light in a third wavelength band different from the second wavelength band, and
wherein the light source is configured to simultaneously emits respective three lights from the first light source, the second light source, and the third light source.

8. The endoscope system according to claim 1,
wherein the second wavelength band has a peak within a range from a wavelength of 400 nm to a wavelength of 585 nm.

9. A method of generating an endoscope image, the method comprising:
receiving, by a color image sensor, light from a subject and generating, by the color image sensor, image pickup signals respectively corresponding to a plurality of different colors;
simultaneously illuminating, by a light source, the subject with light in a first wavelength band having a spectral characteristic of a narrow band having a peak in a range from a wavelength of 585 nm to a wavelength of 615 nm and light in a second wavelength band having a spectral characteristic for making, among a red signal, a green signal, and a blue signal generated based on the image pickup signals respectively corresponding to the plurality of different colors, a pixel value of the red signal smallest;
receiving, by a processor, a selection signal of a specified observation mode; and
in response to receiving the selection signal of the specified observation mode:
   assigning, by the processor, the red signal generated by the color image sensor receiving return light from the subject illuminated with the light in the first wavelength band to a red channel and a green channel of output channels corresponding to the respective colors in a display configured to display a color image; and
   assigning, by the processor, the green signal or the blue signal generated by the color image sensor receiving return light from the subject illuminated with the light in the second wavelength band to a blue channel among the output channels corresponding to the respective colors in the display configured to display the color image.

10. An endoscope system comprising: a color image sensor comprising a red pixel configured to output a red image pickup signal based on light transmitted by a red color filter, a green pixel configured to output a green image pickup signal based on light transmitted by a green color filter, and a blue pixel configured to output a blue image pickup signal based on light transmitted by a blue color filter; a light source configured to simultaneously illuminate a subject with light in a first wavelength band having a spectral characteristic of a narrow band having a peak in a range from a wavelength of 585 nm to a wavelength of 615 nm and light in a second wavelength band having a spectral characteristic of a narrow band having a peak in a range from a wavelength of 400 nm to a wavelength of 585 nm; and a processor configured to receive a selection signal of a specified observation mode; and in response to receiving the selection signal of the specified observation mode: assign a red image signal based on the red image pickup signal generated by the color image sensor receiving returned light from the subject illuminated with the light in the first wavelength band to a red channel configured to output a red component and a green channel configured to output a green component of at each of pixels in a display configured to display a color image; and assign a green image signal based on the green image pickup signal generated by the color image sensor receiving return light from the subject illuminated with the light in the second wavelength band to a blue channel configured to output a blue component at each of the pixels in the display device configured to display the color image.

11. The endoscope system according to claim 10,
wherein the red channel is configured to output a red component, the green channel configured to output a green component, and the blue channel configured to output a blue component at each of the pixels are output channels corresponding to respective colors in the display.

12. The endoscope system according to claim 11,
wherein when assigning the red image signal to the red channel and the green channel in the display, the processor is configured to make a signal value of an image signal assigned to the red channel larger than a signal value of an image signal assigned to the green channel, to enhance a bleeding point in a bleeding region.

13. A system comprising:
a processor configured to:
   receive an image signal comprising a red signal, a green signal and a blue signal generated by an image sensor;
   control a light source to simultaneously illuminate a subject with light in a first wavelength band having a spectral characteristic of a narrow band having a peak in a range from a wavelength of 585 nm to a wavelength of 615 nm and light in a second wavelength band having a spectral characteristic for making a pixel value of the red signal in the image signal smallest;
   receive a selection signal of a specified observation mode; and
   in response to receiving the selection signal of the specified observation mode:
      assign the red signal generated by the image sensor receiving return light from the subject illuminated with the light in the first wavelength band to a red channel and a green channel of output channels corresponding to the respective colors in a display configured to display a color image; and
      assign the green signal or the blue signal generated by the image sensor receiving return light from the subject illuminated with the light in the second wavelength band to a blue channel among the output channels corresponding to respective colors in display configured to display the color image.

* * * * *